(12) United States Patent
Rek (10) Patent No.: US 9,398,938 B2
(45) Date of Patent: Jul. 26, 2016

(54) OSCILLATING DENTAL ANGLE HANDPIECE

(71) Applicant: SDC SWITZERLAND SA, Bioggio (CH)

(72) Inventor: Peter Rek, Pura (CH)

(73) Assignee: SDC SWITZERLAND SA, Bioggio (CH)

( * ) Notice: Subject to any disclaimer, the term of this patent is extended or adjusted under 35 U.S.C. 154(b) by 103 days.

(21) Appl. No.: 14/384,633

(22) PCT Filed: Mar. 12, 2013

(86) PCT No.: PCT/IB2013/051937
§ 371 (c)(1),
(2) Date: Sep. 11, 2014

(87) PCT Pub. No.: WO2013/136262
PCT Pub. Date: Sep. 19, 2013

(65) Prior Publication Data
US 2015/0079540 A1 Mar. 19, 2015

Related U.S. Application Data

(60) Provisional application No. 61/609,799, filed on Mar. 12, 2012.

(51) Int. Cl.
*A61C 1/12* (2006.01)
*A61C 1/14* (2006.01)
*A61C 17/00* (2006.01)
*A61C 15/04* (2006.01)

(52) U.S. Cl.
CPC . *A61C 1/148* (2013.01); *A61C 1/12* (2013.01); *A61C 15/048* (2013.01); *A61C 17/005* (2013.01); *A61C 15/047* (2013.01)

(58) Field of Classification Search
CPC ............ A61C 3/02; A61C 3/03; A61C 17/24; A61C 1/12; A61C 1/14; A61C 1/141; A61C 1/144; A61C 1/148; A61C 1/16
USPC .................................. 433/125, 118, 126, 127
See application file for complete search history.

(56) References Cited

U.S. PATENT DOCUMENTS 4,954,082 A 9/1990 Weissman
5,340,310 A 8/1994 Bifulk
(Continued)

FOREIGN PATENT DOCUMENTS

GB 1211150 11/1970
WO 90/14050 11/1990
WO 2010/095017 8/2010

OTHER PUBLICATIONS

PCT International Search Report mailed on Jul. 25, 2013 for PCT Application PCT/IB2013/051937 filed on Mar. 12, 2013 in the name of SDC Switzerland SA.
(Continued)

*Primary Examiner* — Nicholas Lucchesi
(74) *Attorney, Agent, or Firm* — Steinfl & Bruno LLP (57) ABSTRACT

An oscillating dental angle handpiece for dental tools is described. The handpiece has a hollow housing body, that defines a first longitudinal cavity suitable for coaxially containing inside the first longitudinal cavity a driving shaft, and a second transversal cavity, arranged at an end of the first cavity and having an axis incident with the axis of the first cavity, as well as a driven holder, in which a rotary movement of the driving shaft is transformed into oscillating movement of the driven holder. Additionally, the handpiece is entirely made from synthetic material.

8 Claims, 8 Drawing Sheets

(56) References Cited

U.S. PATENT DOCUMENTS

| | | | |
|---|---|---|---|
| 7,255,559 B2 | 8/2007 | Shen et al. | |
| 7,510,396 B2* | 3/2009 | Lee | A61C 17/005 433/124 |
| 8,123,523 B2* | 2/2012 | Carron | A61C 17/005 433/125 |
| 8,597,022 B2* | 12/2013 | Carron | A61C 17/005 433/114 |
| 9,017,073 B2* | 4/2015 | Madry | A61C 17/24 433/125 |
| 2011/0269102 A1 | 11/2011 | Kuhn et al. | |
| 2012/0258418 A1* | 10/2012 | Shen | A61C 19/066 433/29 |

OTHER PUBLICATIONS

Written Opinion mailed on Jul. 25, 2013 for PCT Application PCT/IB2013/051937 filed on Mar. 12, 2013 in the name of SDC Switzerland SA.

* cited by examiner

OSCILLATING DENTAL ANGLE HANDPIECE

CROSS REFERNCE TO RELATED APPLICATIONS

The present application is the US national stage of International Patent Application PCT/IB2013/051937 filed on Mar. 12, 2013 which, in turn, claims priority to U.S. Provisional Patent Application 61/609/799 filed on Mar. 12, 2012.

The present invention refers to a dental angle handpiece equipped with oscillating movement for dental tools. More specifically, the invention refers to an oscillating dental angle handpiece suitable for being used as a disposable angle handpiece.

There are known oscillating dental handpieces, in other words equipped with an oscillating movement, made from metallic material and therefore not disposable, but rather able to be sterilized before being used again.

These differ from rotary dental handpieces in which a rotary movement is transmitted to dental tools like for example a drill.

Oscillating dental handpieces, on the other hand, transmit an alternating back-and-forth linear oscillating movement to the tool. Non-limiting examples of such tools are files, strips and polishing tools. Such oscillating movement tools are particularly useful in interproximal prophylaxis, restorative or orthodontics treatments.

The purpose of the present invention is to make an oscillating dental angle handpiece that can be used as a disposable angle handpiece.

Another purpose of the present invention is to make an oscillating dental angle handpiece to which it is possible to fix different types of tools.

A further purpose of the present invention is to make an oscillating dental angle handpiece that allows the tools to be oriented.

Another purpose of the present invention is to make an oscillating dental angle handpiece that is particularly simple and functional, with low costs.

These purposes according to the present invention are accomplished by making an oscillating dental angle handpiece as outlined in claim 1.

Further characteristics are provided in the dependent claims.

The characteristics and advantages of an oscillating dental angle handpiece according to the present invention will become clear from the following description, given as an example and not for limiting purposes, referring to the attached schematic drawings, in which.

Figure 1:
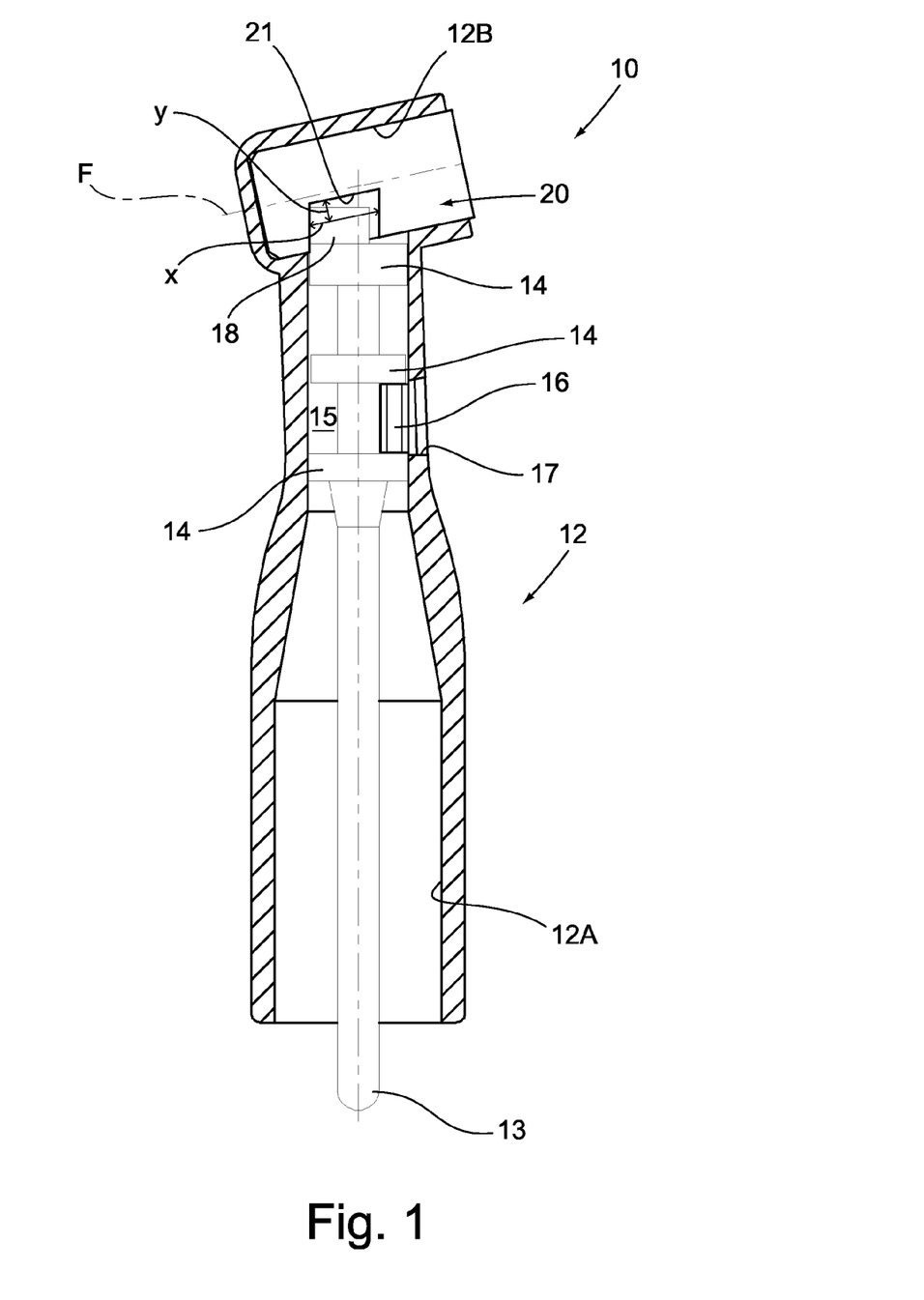
FIG. 1 is a schematic section view showing an oscillating dental angle handpiece for dental tools according to the invention.

With reference to the figures, an oscillating dental angle handpiece equipped with oscillating movement for dental tools is shown wholly indicated with 10 and comprising a hollow housing body 12, that defines a first longitudinal cavity 12A suitable for containing inside it, in a coaxial manner, a driving shaft 13 and a second transversal cavity 12B, 112B, arranged at an end of the first cavity 12A and having its axis incident with the axis of the first cavity 12A, suitable for containing a driven holder 20, schematically shown in FIG. 1, the different variant embodiments of which 20', 20", 20"' and 120 are shown for example in FIGS. 2-9.

The common parts of the angle handpiece 10, described hereafter individually, can on each occasion have the specific components associated with them, which differ according to the various embodiments.

The driving shaft 13 is suitable for being set in rotation by an external micromotor, not shown. Preferably, the transfer of the rotary motion from the micromotor to the driving shaft 13 takes place through an adapter handle 11, shown as an example only in FIG. 5, able to be connected to any of the angle handpieces 10 according to the invention. Alternatively, the angle handpiece 10 could also be directly connected to the micromotor.

Figure 6:
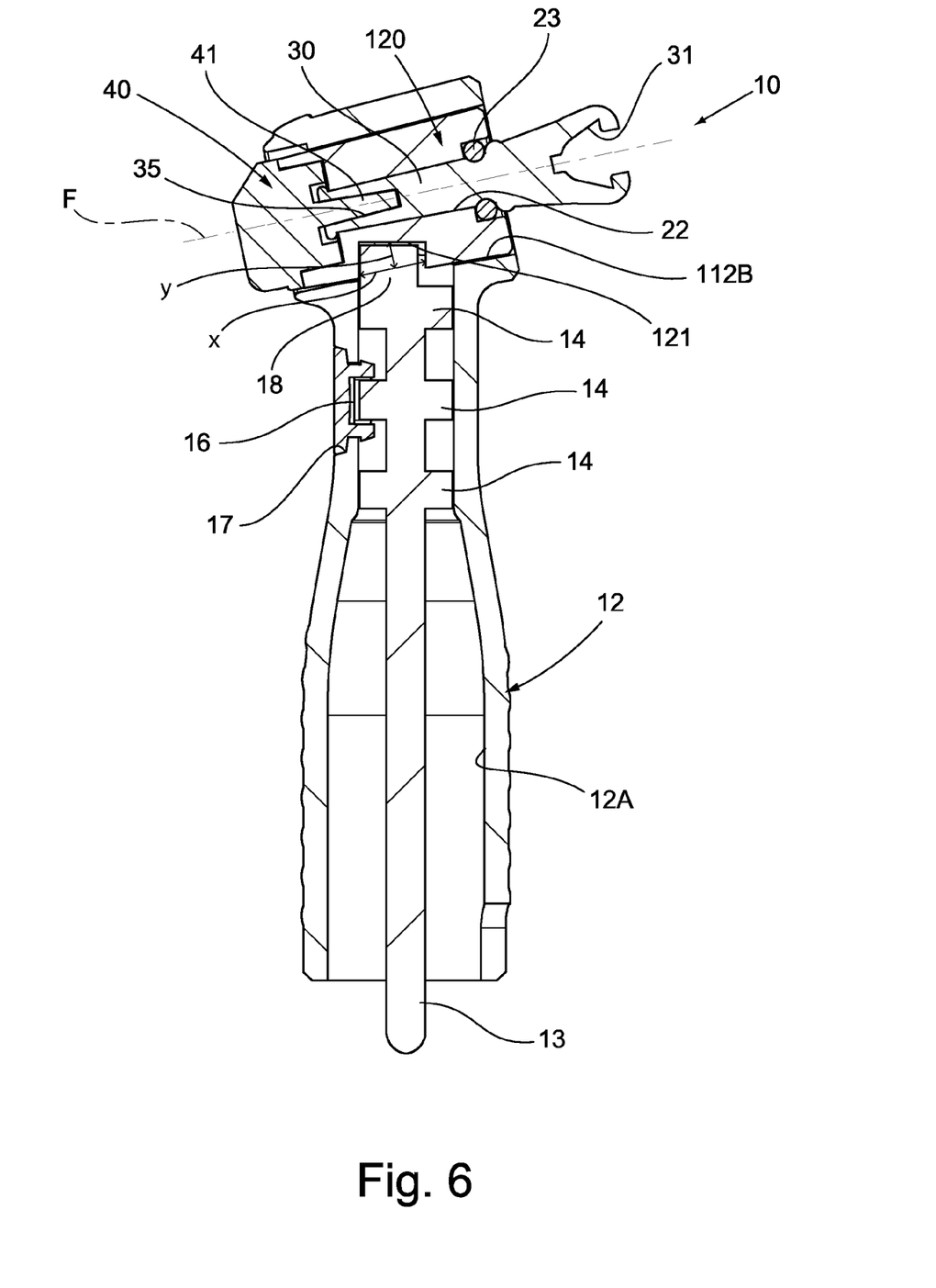
FIG. 6 is a section view showing the oscillating dental angle handpiece of FIG. 5.
Figure 7:
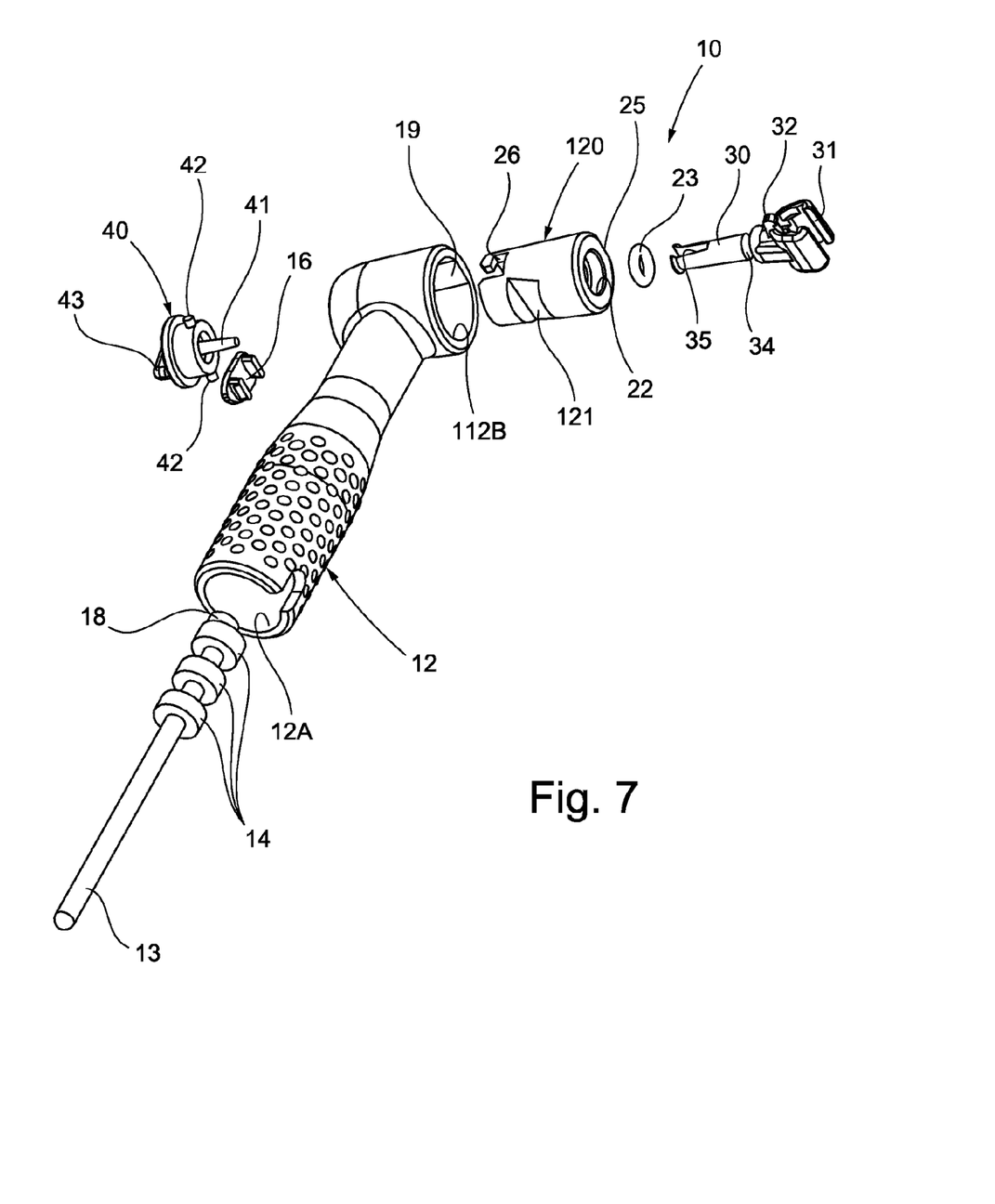
FIG. 7 shows the oscillating dental angle handpiece of FIG. 5 in exploded configuration.
Figure 8:
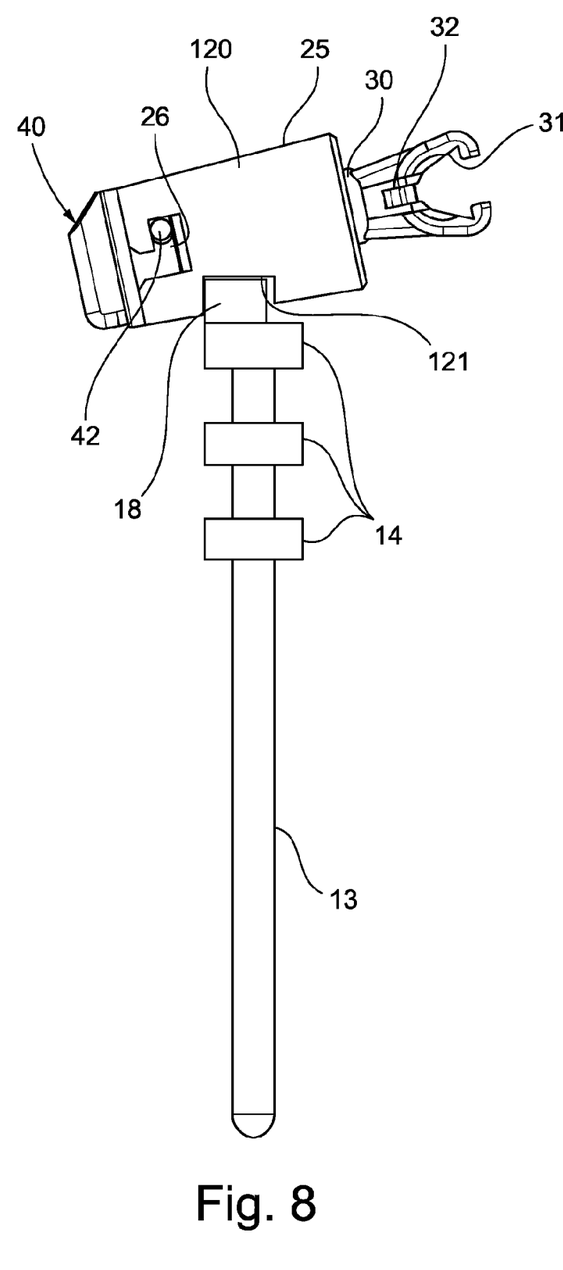
FIGS. 8 and 9 are respective side and rear views of the driving shaft coupled with the holder of the oscillating angle handpiece of FIG. 5.
Figure 9:
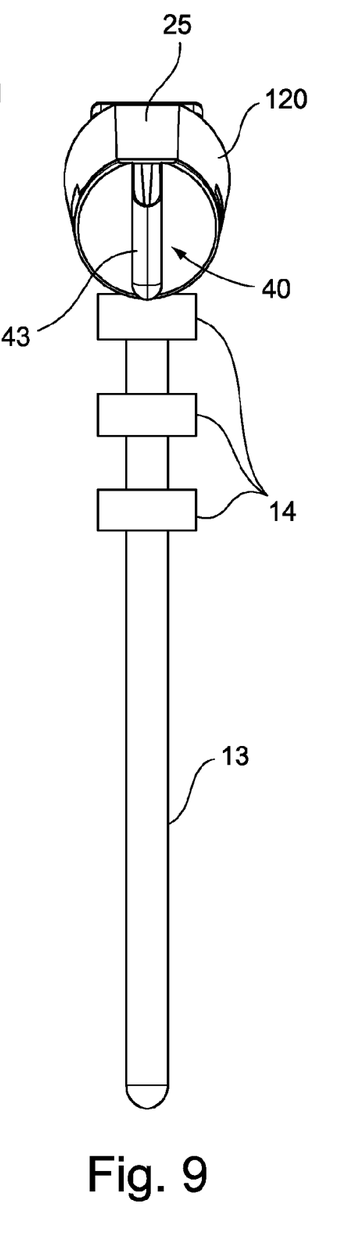

The driving shaft 13 comprises a plurality of annular projections 14, having a diameter slightly smaller than the diameter of the portion of the hollow housing body coupled with them, which keep the driving shaft 13 coaxial with the hollow body 12 during rotation. The annular projections 14 also constitute coupling elements for a locking cap 16, which is positioned in a hole 17 of the hollow body 12 after the axial mounting of the driving shaft 13 in the hollow body 12 to keep the driving shaft 13 axially in position. For example, between two adjacent annular projections 14 there is an annular seat 15 for the engagement of the end of the locking cap 16 (FIGS. 2 and 3) or one of the annular projections 14 themselves is received between two projecting teeth of the locking cap 16 (FIG. 6).

The rotary movement of the driving shaft 13 is transformed into alternating back-and-forth linear oscillating movement of the tool through a cam connection between a cam 18, made in the form of a cylinder arranged at the end of the driving shaft 13 in non-coaxial position, in other words offset with respect to the rotation axis of the driving shaft 13, and the driven holder 20, equipped with a suitable seat 21, 121, having width x slightly greater than the diameter of the cam 18, measured in the direction parallel to the translation axis F of the linear oscillating movement. With the rotation of the driving shaft 13, the cam 18 pulls the driven holder 20 with it, forcing it to carry out an oscillating back-and-forth movement along an axis F.

The driven holder 20 is driven in its oscillating movement by the walls of the second cavity 12B, 112B of the hollow housing body 12, which in the example shown as an example and not for limiting purposes is arranged with a non-perpendicular angle with respect to the axis of the driving shaft 13. In these examples, therefore, the oscillation axis is also arranged with a non-perpendicular angle with respect to the rotation axis of the driving shaft 13.

The handpiece 10 according to the invention generates an alternating linear oscillating movement of the driven holder 20 that can have different lengths, for example comprised between 0.1 mm and 5 mm.

The driven holder 20, according to the invention, is not subject to any rotary movement about the translation axis.

The driven holder 20 is schematically shown in FIG. 1, without the tool itself. The tool can be removably connectable to the driven holder (FIGS. 2, 3 and 5-9) or it can be made as an enbloc with it (FIG. 4).

The angle handpiece 10 is made entirely from synthetic material, for example polycarbonate, polyamide (such as Nylon), PEEK, possibly containing reinforcing fillers.

The angle handpiece made from synthetic material can optionally also be sterilizable, which is not strictly necessary for a disposable angle handpiece.

Figure 2:
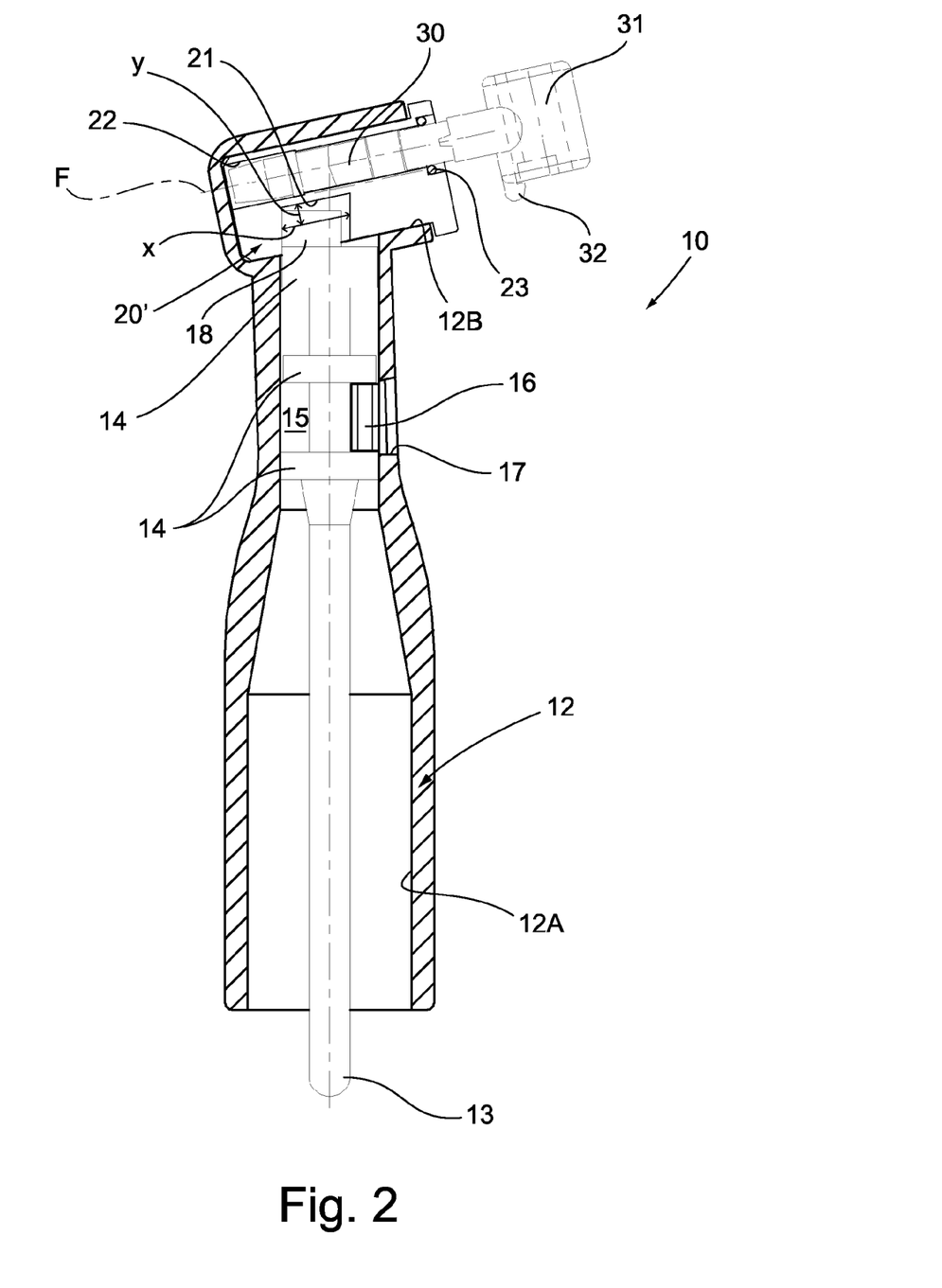
FIG. 2 is a schematic section view showing a first embodiment of an oscillating dental angle handpiece for dental tools according to the invention.

FIG. 2 shows a section of an embodiment of the oscillating angle handpiece 10, coinciding with what is shown and described for the angle handpiece 10 of FIG. 1, equipped with a first embodiment of the driven holder 20' suitable for receiving the tool in a removable manner. The driven holder 20' is provided with a hole 22, parallel to the direction of oscillation, suitable for receiving a shank 30 of a dental tool in removable engagement.

The shank 30 can be made as an enbloc with the tool, according to an example not shown, or, as shown in FIG. 2, it can be suitable for receiving, in removable engagement in a suitable seat 31, a dental tool, non-limiting examples of which are shown in international application WO 2010095017 A1, which should be integrally referred to here. In the embodiment shown in FIG. 2, the engagement seat 31 for the dental tool is further provided with an elastic retaining tooth 32 for snap-locking with the fastening portion of the tool.

The removable shank 30 can be rotated inside its seat, consisting of the hole 22, by 360° in order to orient the dental tool with respect to the most suitable position for the specific dental treatment, according to any desired angle, in other words according to continuous- positions. A retaining ring 23 (O-ring) ensures sufficient friction with respect to the rotation, so that the dental tool, in use, is not subject to rotation with respect to the handpiece 10.

Figure 3:
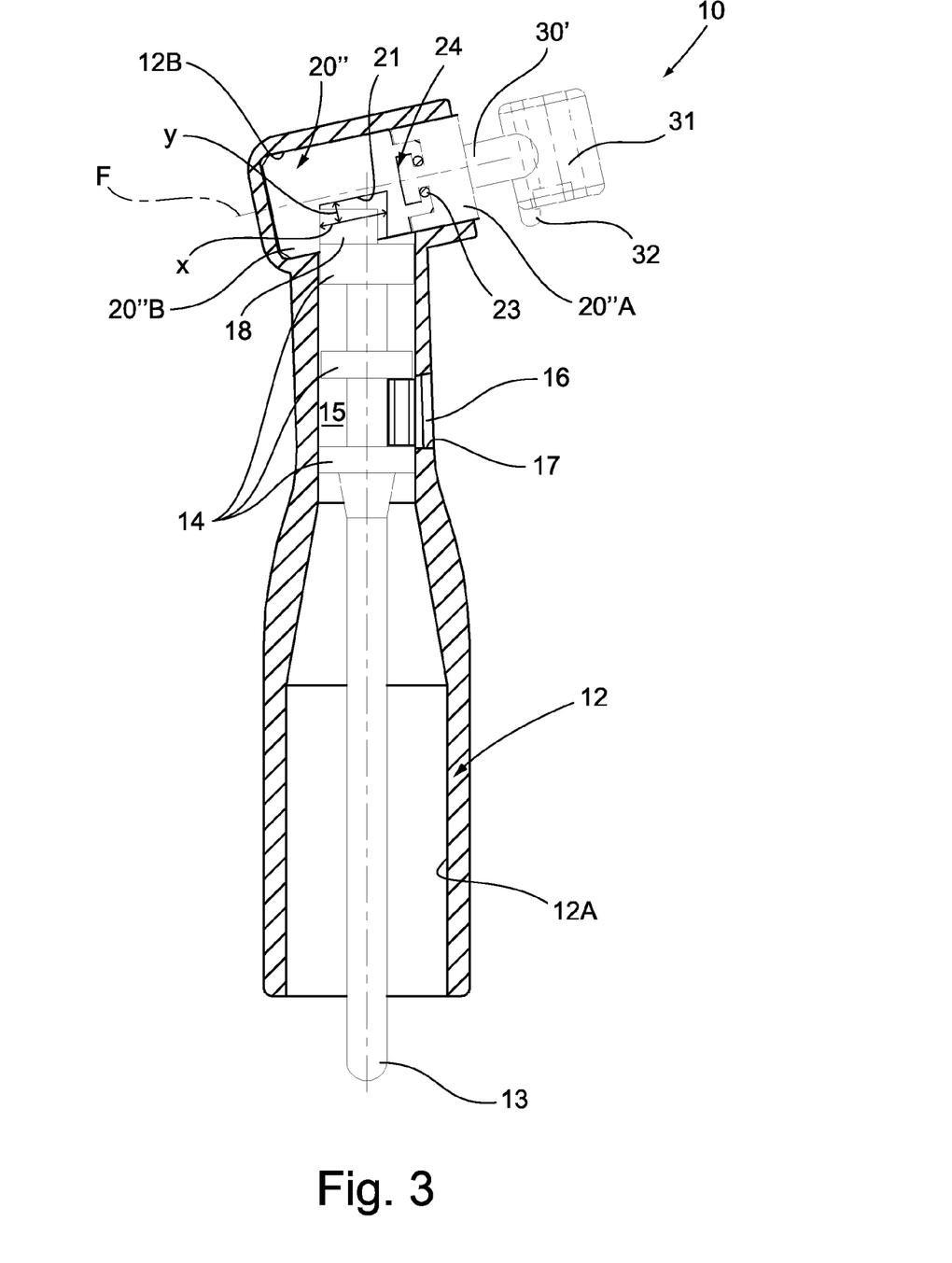
FIG. 3 is a schematic section view showing a second embodiment of an oscillating dental angle handpiece for dental tools according to the invention.
Figure 4:
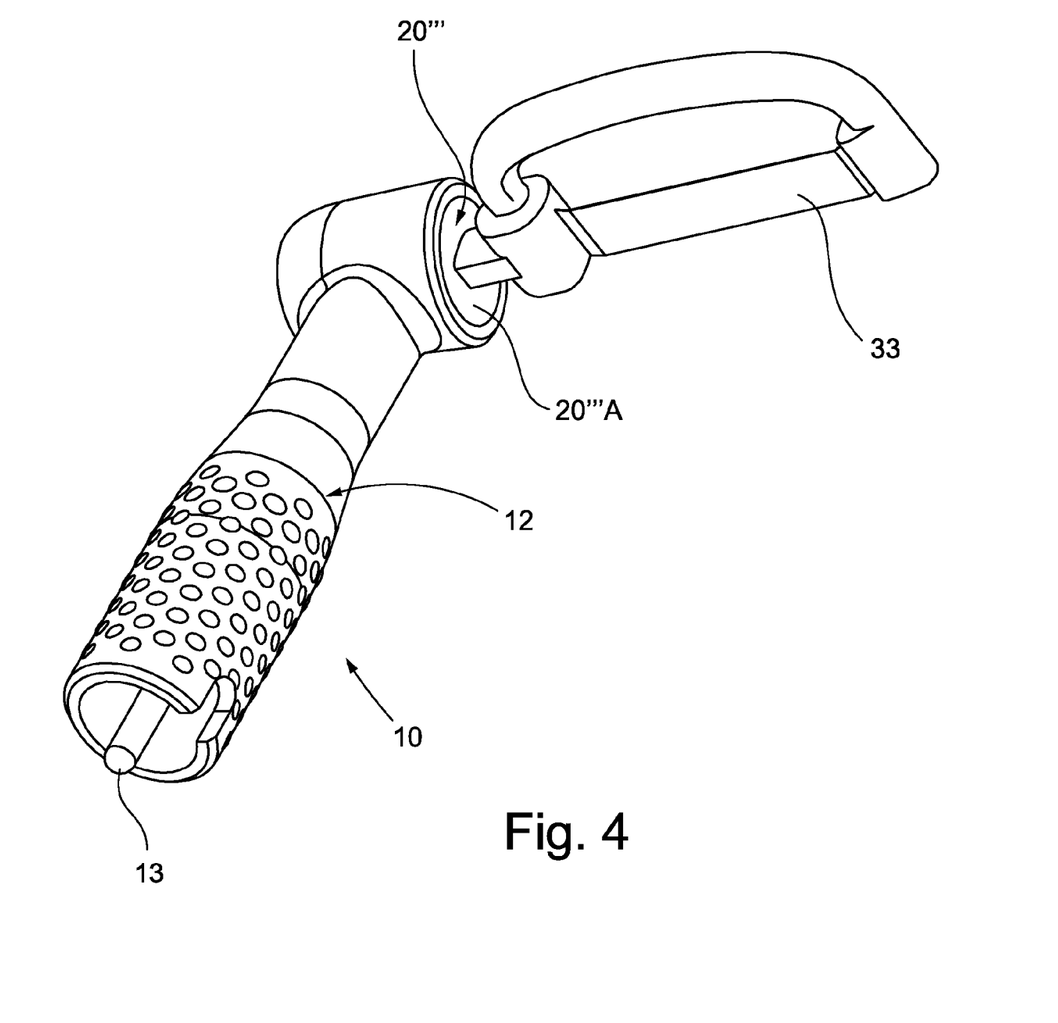
FIG. 4 is a schematic section view showing a third embodiment of an oscillating dental angle handpiece for dental tools according to the invention.
Figure 5:
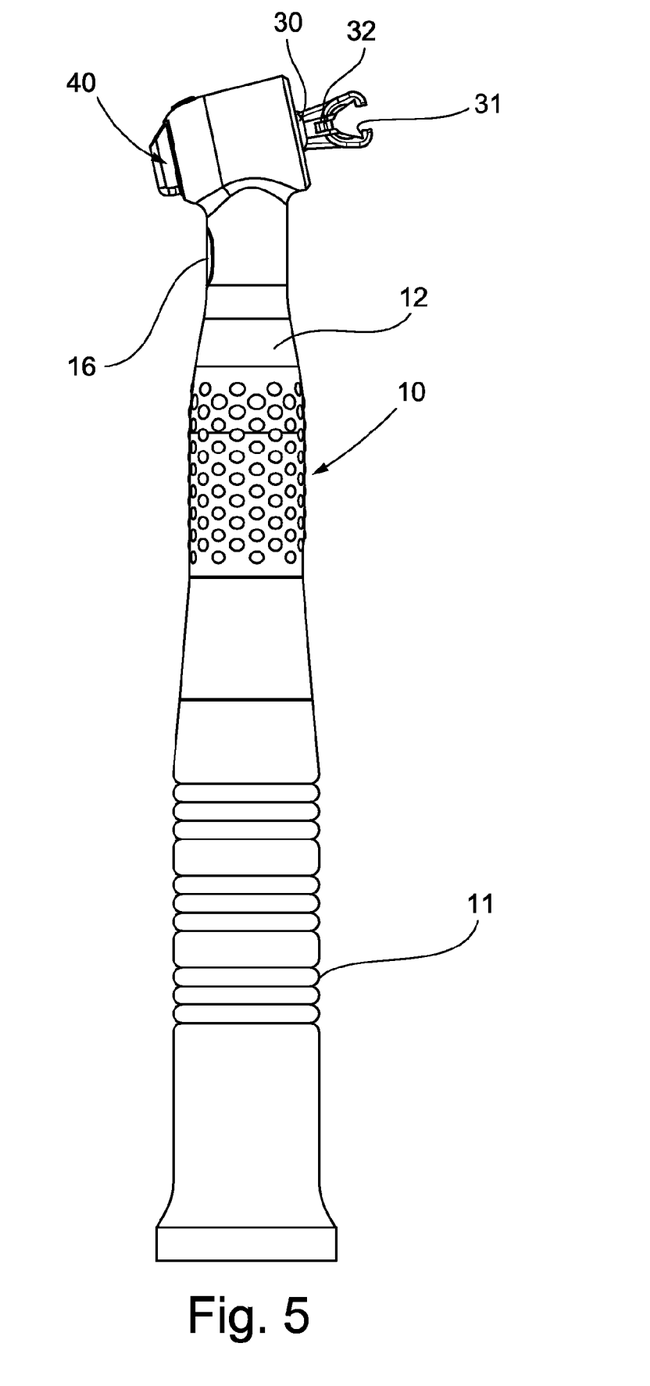
FIG. 5 shows a fourth embodiment of the oscillating dental angle handpiece according to the invention applied to a handle able to be connected to a micromotor.

FIG. 3 shows a section of an embodiment of the oscillating angle handpiece 10, coinciding with what is shown and described for the angle handpiece 10 of FIGS. 1 and 2, equipped with a second embodiment of the driven holder 20" also suitable for removably receiving the tool 33. The driven holder 20" is made in two portions, a front portion 20"A suitable for carrying the tool and a rear portion 20"B coupled with the driving shaft 13. The two portions are connected together through an articulation 24 so as to allow a mutual rotation substantially equal to 360° in order to orient the dental tool with respect to the most suitable position for the specific dental treatment, according to any desired angle, in other words according to continuous positions.

The retaining ring 23, of the O-ring type, positioned near the articulation, ensures sufficient friction with respect to the rotation, so that the dental tool, in use, is not subject to rotation with respect to the handpiece 10.

The front portion 20"A, in the example shown in FIG. 3, comprises a piece of shank 30', made as an enbloc with such a front portion 20"A and equipped with the seat 31 for the removal engagement with a dental tool, of the type described for the embodiment of FIG. 2, in particular equipped with the elastic retaining tooth 32 for the snap-locking with the fastening portion of the tool.

According to a third embodiment of the oscillating handpiece 10 object of the invention, shown in FIG. 4, the driven holder 20''' comprises a front portion 20'''A directly carrying a dental tool 33 made as an enbloc with the angle handpiece 10, in other words not removable with respect to the driven holder 20'''.

According to further variant embodiments of the oscillating angle handpiece according to the invention, not shown, the tool made as an enbloc with the driven holder could have a fixed orientation, in other words not be rotatable about the axis parallel to the direction of oscillation, or such a rotation could be carried out with other equivalent means to the articulation 24 to carry out a continuous or discrete adjustment of the position.

In the embodiments shown as examples and not for limiting purposes in FIGS. 1-4 the driven holder 20', 20", 20''' and the second cavity 12B of the hollow housing body 12 that receives it have a matching cylindrical shape.

According to a fourth preferred embodiment of the angle handpiece 10 object of the invention, the hollow housing body 112B and the driven holder 120 have, along their shell, a matching conical shape, preferable in order to simplify the production by moulding of the pieces made from synthetic material, with the exception of a flat coupling portion parallel to the translation axis F. Indeed, the driven holder 120 has, on the outer shell, a flat portion 25 oriented according to the translation axis F of the linear oscillating movement and arranged on the diametrically opposite side with respect to the seat for the cam 121. The second cavity 112B of the hollow housing body 12 is consequently equipped with a matching plane 19, projecting inside the cavity and also oriented according to the translation axis F of the linear oscillating movement.

The cam 18, according to this embodiment, is received in a seat 121, the height y of which measured in the direction perpendicular to the translation axis F is progressively shorter in the direction of the end with a larger diameter of the conical driven holder 120, in other words at the end suitable for receiving the tool. Indeed, the seat 121 has a bottom wall that when the angle handpiece is mounted is parallel to the front wall of the cam 18 facing it.

This particular coupling between the cam 18 and the seat 121 is selected to act jointly with the coupling between the driven holder 120 and the cavity 112B on a plane parallel to the direction of translation F to ensure that the movement of the tool is exclusively alternating linear oscillating. Indeed, during the rotation of the driving shaft 13, the cam 18 keeps the driven holder 120 constantly in contact with the cavity 112B along the flat coupling. However, the two characteristics could also have application separately.

In the angle handpiece 10 according to the fourth embodiment the hole 22 of the driven holder 120, which receives the shank 30, is made axially centred.

The shank 30 preferably provides a seat 34 for holding the O-Ring 23 and a slit 35 at the opposite end with respect to the engagement seat 31 of the tool for the fixed engagement, of the removable or non-removable type, with the projecting pin 41 of the safety cap 40.

The safety cap 40, which holds the shank 30 in the holder when the angle handpiece 10 is operating, is shown in FIGS. 5-9 in the removable embodiment, but it could also be fixed, thus not allowing the removal of the shank 30 from the driven holder 120.

In the removable version shown, the safety cap 40 comprises two opposite pins 42 suitable for engaging in suitable seats 26 of the driven holder 120 constituting a bayonet locking mechanism. The clockwise or anticlockwise rotation given to the safety cap 40 acting on an external grip element 43 allows the locking or the release of the bayonet mechanism.

The oscillating dental angle handpiece 10 according to the invention can be combined with any dental tool to be moved with oscillating motion, like for example files, strips, and polishing tools. The tools described and shown should be taken as examples and not for limiting purposes.

The oscillating dental angle handpiece 10 according to the invention is assembled by firstly inserting the driven holder 20, 20', 20", 20'", 120 inside the second cavity 12B, 112B of the hollow housing body 12 and then axially introducing the driving shaft 13 inside the first cavity 12A of the hollow housing body 12 until the cam 18 is introduced into the seat 21. The locking cap 16 inserted from the outside into the hole 17 of the hollow housing body 12 and engaged in the annular seat 15 determines the stable axial positioning of the driving shaft 13 in the hollow housing body 12. The annular configuration of the seat 15 allows the relative rotation between the driving shaft 13 and the hollow housing body 12.

For angle handpieces 10 equipped with a shank 30 made as a separate piece, it is thus inserted in the driven holder and removably or fixedly coupled with it.

The oscillating dental angle handpiece according to the present invention has the advantage of being made entirely from plastic. Therefore, advantageously, the oscillating dental angle handpiece according to the invention is suitable for being used as a disposable angle handpiece.

A further advantage consists of the possibility of easily replacing the driven holder to allow the operator to select the type of fastening of the dental tool that is preferred on each occasion, keeping the other components of the oscillating angle handpiece unchanged. As a result it has great versatility with respect to the possible combinations without penalizing the number of single components to be bought by the operator and to be kept in storage.

The oscillating dental angle handpiece according to the invention is also advantageously equipped with exclusively alternating linear oscillating movement that allows the maximum precision in carrying out dental treatment.

The oscillating angle handpiece thus conceived can undergo numerous modifications and variants, all of which are covered by the invention; moreover, all of the details can be replaced by technically equivalent elements. In practice, the materials used, as well as the sizes, can be whatever according to the technical requirements.

The invention claimed is:

1. An oscillating dental angle handpiece for dental tools, comprising:
    a hollow housing body defining a first longitudinal cavity configured to internally contain, in a coaxial manner, a driving shaft and a second transversal cavity, arranged at an end of said first cavity and having a second cavity axis incident with a first cavity axis,
    an interchangeable driven holder, said driven holder comprising an axially centered hole, parallel to an oscillation direction of the oscillating dental angle handpiece, the axially centered hole being removably engaged with a shank of a dental tool according to a coupling orientable in discrete and continuous positions, said shank comprising a slit at an opposite end of the shank with respect to the dental tool, and
    a safety cap comprising a projecting pin, the projecting pin fixedly engaging in a removable or non-removable manner with said slit of said shank,
    wherein rotary motion of said driving shaft is transformed into oscillating motion of said driven holder, and wherein said angle handpiece is made entirely from synthetic material.

2. The angle handpiece according to claim 1, further comprising a cylinder-shaped cam arranged at an end of the driving shaft in a position not coaxial with the driving shaft, said cylinder-shaped cam defining a cam connection between the cam and a seat of the driven holder, the seat having a width, measured in a direction parallel to a translation axis of the oscillating motion of the dental angle handpiece, said width being slightly greater than a diameter of said cylinder-shaped cam, said cam connection transforming said rotary motion into said oscillating motion.

3. The angle handpiece according to claim 2, wherein said seat has a height, measured in a direction perpendicular to the translation axis, decreasing towards the dental tool shank.

4. The angle handpiece according to claim 2, wherein said hollow housing body and said driven holder have a matching conical shape along their shell except for a flat coupling portion arranged parallel to the translation axis, on a diametrically opposite side of said driven holder with respect to said seat for the cylinder-shaped cam.

5. The angle handpiece according to claim 1, further comprising a retaining ring between said hole and said shank to allow orientation of said coupling according to continuous positions.

6. The angle handpiece according to claim 1, further comprising a bayonet locking mechanism to removably connect said cap to said driven holder.

7. The angle handpiece according to claim 1, wherein said driving shaft comprises a plurality of annular projections, each having a slightly smaller diameter than the diameter of a portion of said hollow housing body coupled with them, said annular projections also forming coupling elements for a locking cap positioned in a hole of said hollow body.

8. The angle handpiece according to claim 1, wherein said synthetic material is a sterilizable synthetic material.

* * * * *